US008007173B2

(12) United States Patent
Paidi et al.

(10) Patent No.: US 8,007,173 B2
(45) Date of Patent: Aug. 30, 2011

(54) CALIBRATION OF IMAGING GEOMETRY PARAMETERS

(75) Inventors: Ajay Paidi, Pleasant Hill, CA (US); Jonathan S. Maltz, Oakland, CA (US); Supratik Bose, Walnut Creek, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 139 days.

(21) Appl. No.: 12/579,252

(22) Filed: Oct. 14, 2009

(65) Prior Publication Data

US 2011/0085645 A1    Apr. 14, 2011

(51) Int. Cl.
*G01D 18/00*    (2006.01)
(52) U.S. Cl. ....................................................... 378/207
(58) Field of Classification Search ............ 378/62, 378/65, 98.11, 98.12, 207; 382/130–132
See application file for complete search history.

(56) References Cited

U.S. PATENT DOCUMENTS

2007/0122020 A1 *    5/2007    Claus et al. ................... 382/131

* cited by examiner

*Primary Examiner* — Courtney Thomas

(57) ABSTRACT

Some embodiments include determination of a first projection image of a phantom based on first imaging geometry parameters associated with a first radiation-based imaging system and on a virtual model of the phantom, acquisition of a second projection image of the phantom based on radiation emitted from the first radiation-based imaging system, the phantom located at a first position and determination of a difference between the first projection image and the second projection image. Second imaging geometry parameters are determined based on the first imaging geometry parameters and the difference between the first projection image and the second projection image, a third projection image of the phantom is determined based on the second imaging geometry parameters and on the virtual model of the phantom, and a fourth projection image of the phantom located at the first position is acquired based on radiation emitted from the first radiation-based imaging system. A difference between the third projection image and the fourth projection image is determined and it is determined that the difference between the third projection image and the fourth projection image is less than a threshold.

20 Claims, 7 Drawing Sheets

CALIBRATION OF IMAGING GEOMETRY PARAMETERS

BACKGROUND

1. Field

The embodiments described herein relate generally to radiation-based imaging systems. More particularly, the described embodiments relate to calibration of radiation-based imaging systems used in conjunction with radiation therapy.

2. Description

A linear accelerator produces electrons or photons having particular energies. In one common application, a linear accelerator generates a radiation beam and directs the beam toward a target area of a patient. The beam is intended to destroy cells within the target area by causing ionizations within the cells or other radiation-induced cell damage.

Radiation treatment plans are intended to maximize radiation delivered to a target while minimizing radiation delivered to healthy tissue. To design a radiation treatment plan, a designer must assume that relevant portions of a patient will be in particular positions relative to a linear accelerator during delivery of the treatment radiation. The goals of maximizing target radiation and minimizing healthy tissue radiation may not be achieved if the relevant portions are not positioned in accordance with the treatment plan during delivery of the radiation. More specifically, errors in positioning the patient can cause the delivery of low radiation doses to tumors and high radiation doses to sensitive healthy tissue. The potential for misdelivery increases with increased positioning errors.

Conventional imaging systems may be used to verify patient positioning prior to and during the delivery of treatment radiation. Specifically, this verification is intended to confirm that relevant portions of a patient are positioned in accordance with a treatment plan. Some systems may generate, for example, a two-dimensional projection image of a patient portal by passing a radiation beam through the patient and receiving the exiting beam at an imaging system (e.g., a flat panel imager). Other systems produce three-dimensional megavoltage cone beam computed tomography (MV CBCT) images and/or three-dimensional kilovoltage cone beam computed tomography (kV CBCT) images of a patient volume prior to and/or during radiation delivery thereto. Recently-developed systems include linear/arc tomosynthesis and stationary tomosynthesis, which provide three-dimensional images based on fewer projection images than required by CBCT, but usually at poorer resolution.

In this regard, the three-dimensional images mentioned above are reconstructed from projection images using known reconstruction algorithms. The reconstruction algorithms may differ depending on the particular system used to obtain the projection images. However, each reconstruction algorithm requires knowledge of the imaging geometry parameters which were in effect during acquisition of the projection images. Imaging geometry parameters may include, but are not limited to, position of x-ray source(s), position of flat panel detector, panel tilt, panel sag, etc.

Imaging geometry parameters are calculated for an imaging system during a calibration procedure. During a typical calibration procedure, a projection image of a known phantom is acquired by the imaging system. Features within the phantom (e.g., embedded fiducials) are recognized within the projection image using feature-recognition techniques. The imaging geometry parameters are then calculated based on the locations of the features within the projection image. The manner of calculation is dependent upon the particular source-detector trajectory of the imaging system.

The above-described feature recognition and imaging geometry parameter calculation can be time-consuming and processor-intensive. Moreover, and particularly relevant to systems including more than one imaging system, the required phantom, phantom location, and/or imaging geometry parameter calculation may differ depending on the type of imaging system being calibrated.

Systems are therefore desired for efficient determination of imaging geometry parameters. Such systems may be useful for calibrating multiple imaging systems and/or multiple types of imaging systems.

SUMMARY

In order to address the foregoing, some embodiments provide a system, method, apparatus, and means to determine a first projection image of a phantom based on first imaging geometry parameters associated with a first radiation-based imaging system and on a virtual model of the phantom, acquire a second projection image of the phantom based on radiation emitted from the first radiation-based imaging system, the phantom located at a first position, and determine a difference between the first projection image and the second projection image.

Second imaging geometry parameters are determined based on the first imaging geometry parameters and the difference between the first projection image and the second projection image, a third projection image of the phantom is determined based on the second imaging geometry parameters and on the virtual model of the phantom, a fourth projection image of the phantom located at the first position is acquired based on radiation emitted from the first radiation-based imaging system, a difference between the third projection image and the fourth projection image is determined, and it is determined that the difference between the third projection image and the fourth projection image is less than a threshold.

Some aspects further include, for a second radiation-based imaging system, determining a fifth projection image of the phantom based on third imaging geometry parameters associated with the second radiation-based imaging system and on the virtual model of the phantom, acquiring a sixth projection image of the phantom based on radiation emitted from the second radiation-based imaging system, the phantom located at the first position, and determining a difference between the fifth projection image and the sixth projection image.

Fourth imaging geometry parameters are determined based on the third imaging geometry parameters and the difference between the fifth projection image and the sixth projection image, a seventh projection image of the phantom is determined based on the fourth imaging geometry parameters and on the virtual model of the phantom, an eighth projection image of the phantom located at the first position is acquired based on radiation emitted from the second radiation-based imaging system, a difference between the seventh projection image and the eighth projection image is determined, and it is determined that the difference between the seventh projection image and the eighth projection image is less than a second threshold.

The appended claims are not limited to the disclosed embodiments, however, as those in the art can readily adapt the descriptions herein to create other embodiments and applications.

BRIEF DESCRIPTION OF THE DRAWINGS

Embodiments will become readily apparent from consideration of the following specification as illustrated in the accompanying drawings, in which like reference numerals designate like parts, and wherein.

DETAILED DESCRIPTION

The following description is provided to enable a person in the art to make and use some embodiments and sets forth the best mode contemplated by the inventors for carrying out some embodiments. Various modifications, however, will remain readily apparent to those in the art.

Figure 1:
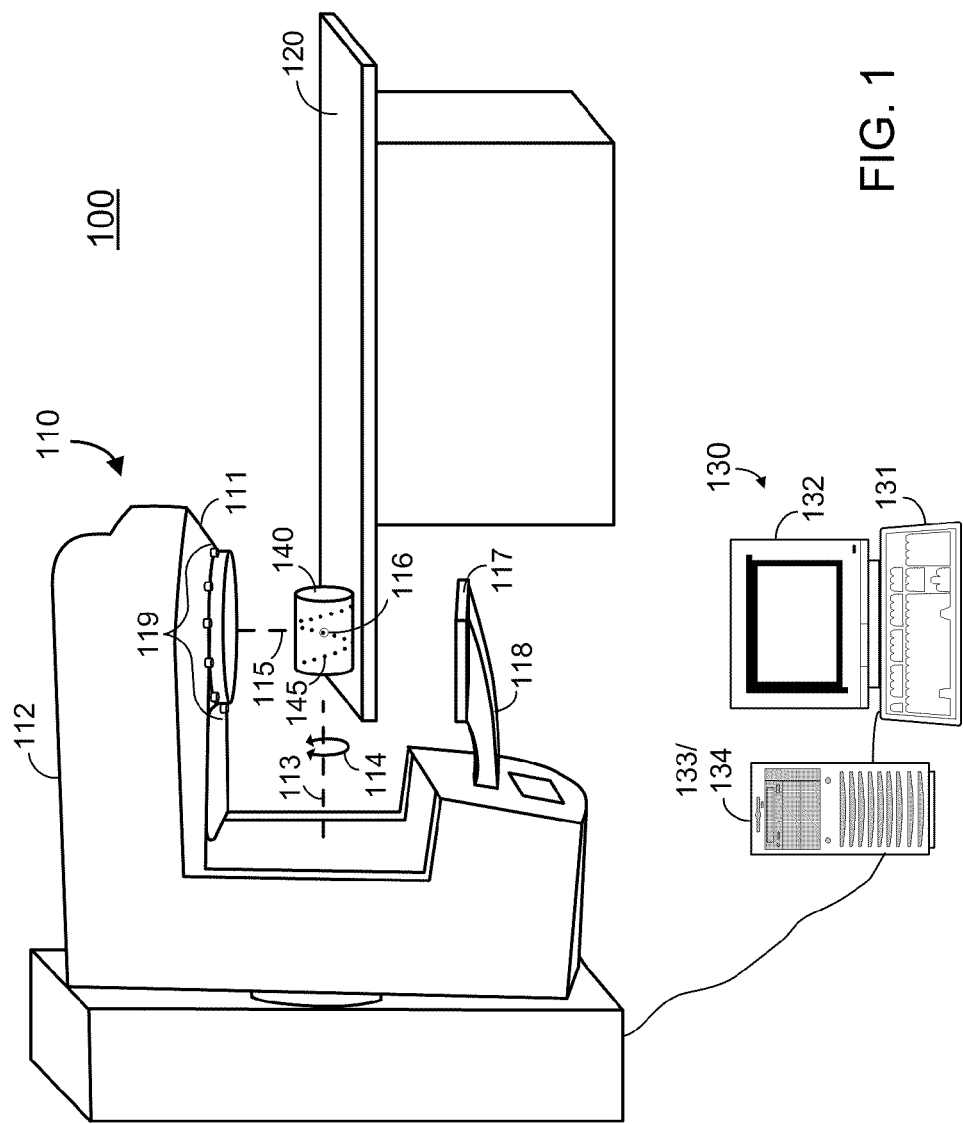
FIG. 1 is a perspective view of a linear accelerator system according to some embodiments.

FIG. 1 illustrates radiation treatment room 100 pursuant to some embodiments. Radiation treatment room 100 includes linear accelerator (linac) 110, table 120 and operator console 130. The elements of radiation treatment room 100 may be used to deliver a beam of x-rays to a target volume such as phantom 140. Of course, the target volume may comprise a patient positioned to receive the beam according to a radiation treatment plan. The elements of treatment room 100 may be employed in other applications according to some embodiments.

Linac 110 may comprise an in-line kilovoltage/megavoltage radiotherapy delivery system such as the ARTISTE™ system from Siemens Medical Solutions USA, Inc. but embodiments are not limited thereto. Linac 110 generates and emits an x-ray beam from treatment head 111. The radiation beam may comprise electron, photon or any other type of radiation. According to some embodiments, the beam exhibits energies in the megavoltage range (i.e. >1 MeV) and may therefore be referred to as megavoltage beam. The x-ray beam may be used for treatment and, in some embodiments, may be used to acquire an MV CBCT image. Accordingly, treatment head 111 may be considered a radiation-based imaging system.

Also included within treatment head 111 is a beam-shielding device, or collimator, for shaping the beam and for shielding sensitive surfaces from the beam. The collimator may be rotated and various elements of the collimator may be positioned according to a treatment plan. The collimator may thereby control a cross-sectional shape of the beam.

Treatment head 111 is coupled to a projection of gantry 112. Gantry 112 is rotatable around gantry axis 113 before, during and after radiation treatment. As indicated by arrow 114, gantry 112 may rotate clockwise or counter-clockwise according to some embodiments. Rotation of gantry 112 serves to rotate treatment head 111 around axis 113.

During radiation treatment or calibration, treatment head 111 emits a divergent beam of megavoltage x-rays along beam axis 115. The beam is emitted towards isocenter 116 of linac 110. Isocenter 116 is located at the intersection of beam axis 115 and gantry axis 113. Due to divergence of the beam and the shaping of the beam by the aforementioned beam-shaping devices, the beam may deliver radiation to a volume of phantom 140 rather than only through isocenter 116.

Table 120 supports phantom 140 during calibration and may support a patient during radiation treatment. Table 120 may be adjustable to assist in positioning phantom 140 or a particular volume of a patient at isocenter 116. Table 120 may also be used to support devices used for such positioning, for calibration and/or for verification.

Imaging device 117 may comprise any system to acquire an image based on received x-rays. Imaging device 117 may be attached to gantry 112 in any manner, including via extendible and retractable housing 118. Rotation of gantry 112 may cause treatment head 111 and imaging device 117 to rotate around isocenter 116 such that isocenter 116 remains located between treatment head 111 and imaging device 117 during the rotation.

Imaging device 117 may acquire projection images before, during and/or after radiation treatment. For example, imaging device 117 may be used to acquire images based on radiation emitted from treatment head 111. These images may reflect the attenuative properties of objects located between treatment head 111 and imaging device 117. As will be described below, such projection images may be used to determine imaging geometry parameters associated with the imaging system consisting of treatment head 111 and imaging device 117. The projection images and/or three-dimensional images reconstructed based thereon may also be used to verify and record a target volume position and a position of an internal patient portal to which radiation is delivered.

X-ray sources 119 are elements of a stationary tomosynthesis imaging system. X-ray sources 119 are disposed in a plane perpendicular to axis 115 and are arranged in a circular configuration, but embodiments are not limited thereto. In this regard, x-ray sources 119 may comprise any geometrical arrangement and operate in any manner, including those described in commonly-assigned co-pending applications, and in Fixed Gantry Tomosynthesis System For Radiation Therapy Image Guidance Based On A Multiple Source X-Ray Tube With Carbon Nanotube Cathodes, Maltz et al., Med. Phys. 36 (5), May 2009, pp. 1624-1636.

X-ray sources 119 may comprise any sources to emit kilovoltage radiation or other imaging radiation that are or become known. In some embodiments, x-ray sources 119 employ cathodes based on carbon nanotube or thermionic emission technology. X-ray sources 119 are affixed to gantry 112 such that each x-ray source 119 is disposed in a fixed relationship to each other x-ray source 119. Moreover, in some embodiments, each x-ray source 119 is disposed in a fixed relationship with respect to treatment head 111.

Imaging device 117 may be used to acquire a projection image based on radiation emitted from each one of x-ray sources 119. Again, these images may reflect the attenuative properties of objects located between x-ray sources 119 and imaging device 117. These projection images may be used to determine imaging geometry parameters associated with the imaging system consisting of x-ray sources 119 and imaging device 117. It is noted that the source-detector trajectory of this imaging system differs from the source-detector trajectory of the imaging system consisting of treatment head 111 and imaging device 117, although isocenter 116 is an isocenter of both systems. As before, the projection images (and/or three-dimensional reconstructions based thereon)

may also be used to verify and record a target volume position and a position of an internal patient portal to which radiation is delivered.

Operator console 130 includes input device 131 for receiving instructions from an operator such as an instruction to calibrate linear accelerator 110 and an instruction to deliver treatment radiation according to a treatment plan. Console 130 also includes output device 132, which may be a monitor for presenting calculated projection images, acquired projection images, three-dimensional images, operational parameters of linear accelerator 110 and/or interfaces for controlling elements thereof. Input device 131 and output device 132 are coupled to processor 133 and storage 134.

Processor 133 executes program code according to some embodiments. The program code may be executable to control linear accelerator 110 to operate as described herein. The program code may be stored in storage 134, which may comprise one or more storage media of identical or different types, including but not limited to a fixed disk, a floppy disk, a CD-ROM, a DVD-ROM, a Zip™ disk, a magnetic tape, and a signal. Storage 134 may store, for example, virtual models of phantoms, initial imaging geometry parameters, radiation treatment plans, projection images, software applications to calibrate linear accelerator 110 and/or to provide radiation treatment, and other data used to perform radiation treatment.

Operator console 130 may be located apart from linear accelerator 110, such as in a different room, in order to protect its operator from radiation. For example, linear accelerator 110 may be located in a heavily shielded room, such as a concrete vault, which shields the operator from radiation generated by accelerator 110.

Each of the devices shown in FIG. 1 may include less or more elements than those shown. In addition, embodiments are not limited to the devices shown in FIG. 1.

Figure 2:
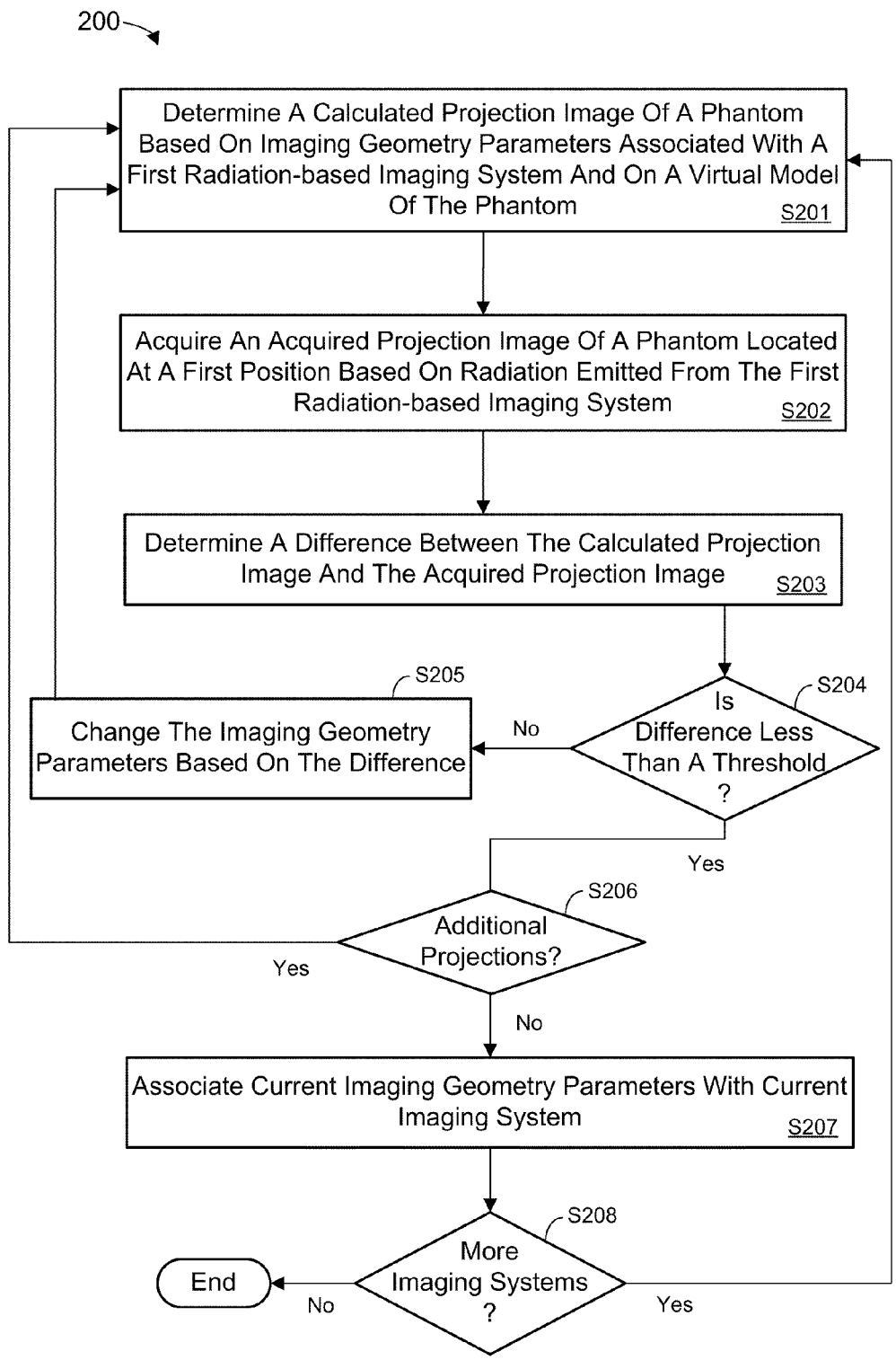
FIG. 2 is a flow diagram of process steps pursuant to some embodiments.

FIG. 2 is a flow diagram of a process according to some embodiments. Process 200 and the other processes described herein may be performed using any suitable combination of hardware, software or manual means. Software embodying these processes may be stored by any medium, including a fixed disk, a floppy disk, a CD-ROM, a DVD-ROM, a Zip™ disk, a magnetic tape, or a signal. Examples of these processes will be described below with respect to the elements of treatment room 100, but embodiments are not limited thereto.

Process 200 may be performed at any time, including during initial installation of linear accelerator 110 in treatment room 100. Process 200 may be performed periodically according to a Quality Assurance schedule, and/or prior to each radiation treatment fraction.

In some embodiments, and prior to S201, an operator may manipulate input device 131 of operator console 130 to initiate operation of linear accelerator 110. In response, processor 133 may execute program code of a system control application stored in storage 134. The operator may then operate input device 131 to initiate a calibration procedure to determine imaging geometry parameters of the imaging system comprising treatment head 111 and imaging device 117.

At S201, a calculated projection image of a phantom is determined. The calculated projection image is determined based on a virtual model of the phantom and on imaging geometry parameters associated with a first radiation-based imaging system.

According to the present example of process 200, a calculated projection image of phantom 140 is determined at S201 based on imaging geometry parameters associated with the imaging system consisting of treatment head 111 and imaging device 117. Storage 134 may store initial (or model) imaging geometry parameters associated with this imaging system. Using known techniques, a projection matrix may be created at S201 for a particular projection angle based on the initial imaging geometry parameters.

Storage 134 may store a virtual model of phantom 140. Phantom 140 comprises an x-ray transparent cylinder including embedded fiducial markers 145 (e.g., tungsten beads). The virtual model indicates at least the locations of a portion of fiducial markers 145 in relation to a point of phantom 140. To determine the calculated projection image for a projection angle, the model is forward-projected onto imaging system 117 based on the projection matrix for that projection angle and using known forward-projection techniques. This forward projection may assume that the point of (virtual) phantom 140 is located at isocenter 116.

Figure 3:
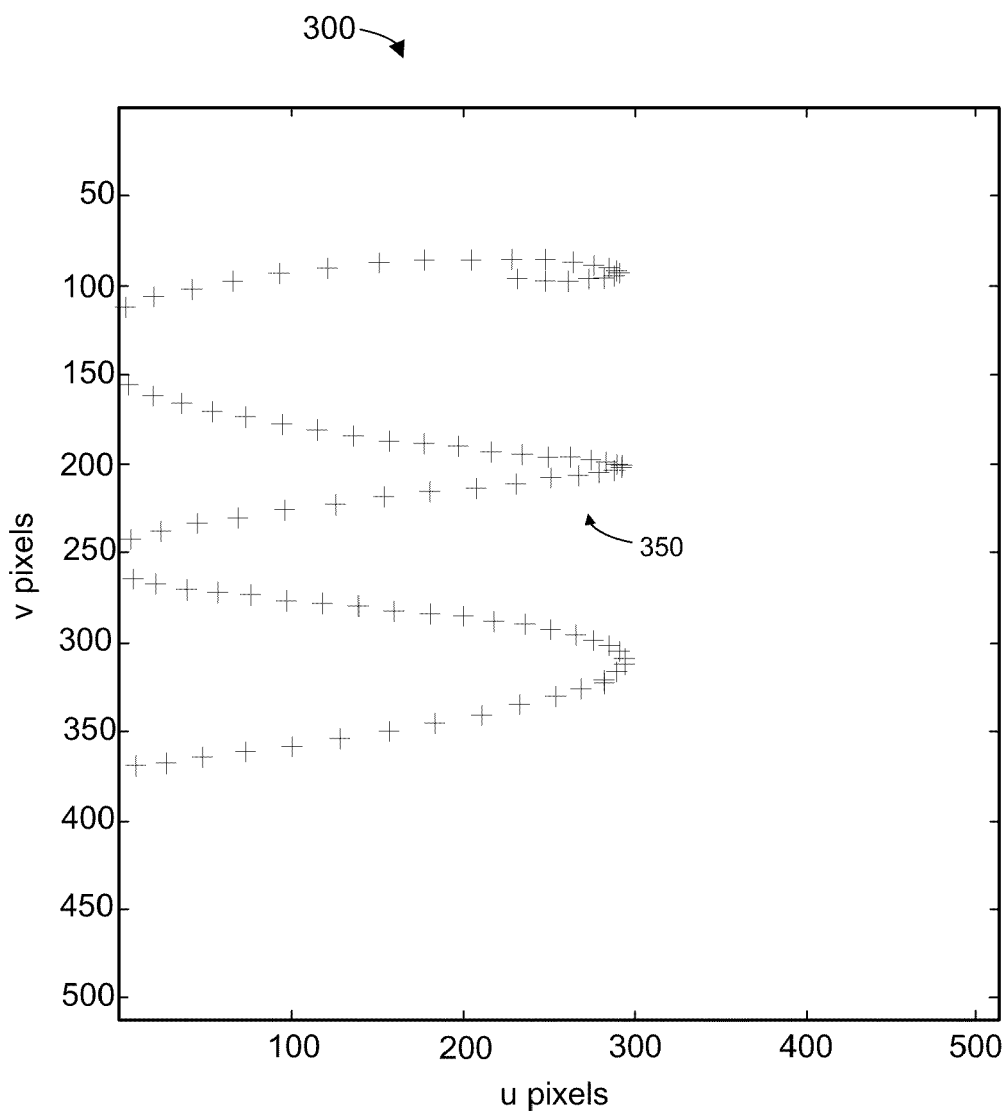
FIG. 3 is a representation of a calculated projection image according to some embodiments.

FIG. 3 is a representation of calculated projection image 300 determined at S201 according to some embodiments. Calculated projection image 300 includes pixels 350 associated with markers 145 of phantom 140. Embodiments are not limited to phantom 140 or to the arrangement of markers 145.

Next, at S202, an acquired projection image of the phantom is acquired using the first radiation-based system. The projection image is acquired from the projection angle associated with the projection matrix used to determine the calculated projection image. Similarly, the phantom is located at a first position which may correspond to the position in which the virtual phantom was assumed to reside during determination of the calculated projection image. More specifically, if the calculated projection image was determined based on a particular positioning of the virtual model with respect to isocenter 116, phantom 140 is positioned in the same manner with respect to isocenter 116 prior to acquisition of the acquired projection image.

Figure 4:
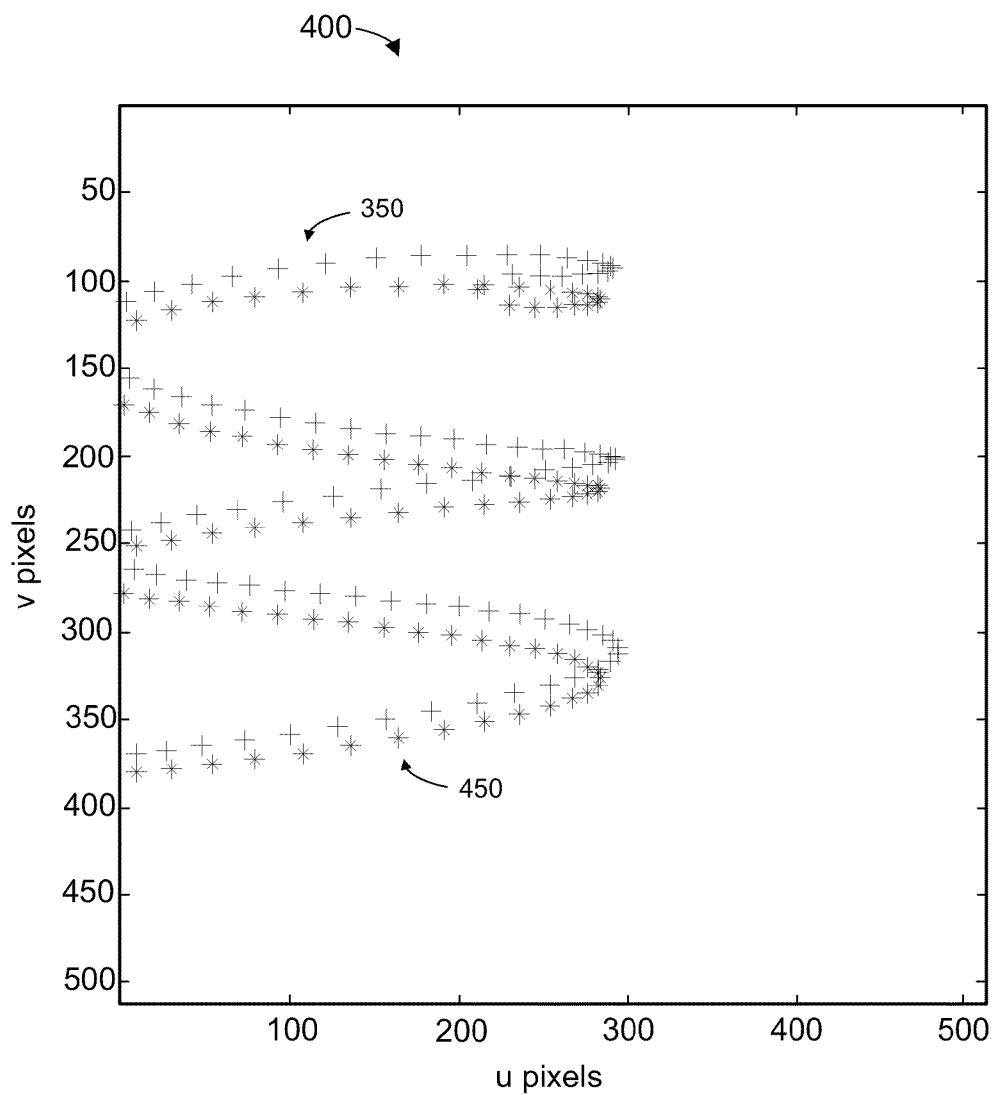
FIG. 4 is a representation of the FIG. 3 calculated projection image and a corresponding acquired projection image according to some embodiments.

Acquisition of the acquired projection image may include emitting a radiation beam from treatment head 111 and detecting radiation received by imaging device 117. FIG. 4 shows projection image 400 including pixels 450 indicating the locations of markers 145. For comparison, pixels 350 of projection image 300 are superimposed thereon.

A difference between the calculated projection image and the acquired projection image is determined at S203. The difference may be determined by processor 133 using any system for image comparison that is or becomes known. If, at S204, the difference is not determined to be less than a predetermined threshold value, the initial imaging geometry parameters are changed at S205 based on the difference.

According to some embodiments, the initial imaging geometry parameters are changed in an attempt to minimize the difference between the calculated projection image and the acquired projection image. Changing the initial imaging geometry parameters may comprise perturbing the parameters using a feedback loop which takes the difference as an input. According to some embodiments, the imaging geometry parameters are changed using non-linear optimization techniques. For example, S205 may comprise changing the imaging geometry parameters to try and minimize the function $\Sigma_{u,v}[f_a(u,v)-f_m(u,v)]^2$, where $(u, v)$ are image pixel coordinates, $f_m(u,v)$ is the calculated projection image, and $f_a(u,v)$ is the acquired projection image.

Flow returns to S201 to determine a new calculated projection image based on the changed imaging geometry parameters and on the virtual model of the phantom. Referring back to the prior example of S201, a changed projection matrix may be generated for the particular projection angle based on the changed imaging parameters, and the virtual model of the phantom is forward-projected to imaging device 117 based on the changed projection matrix.

Figure 5:
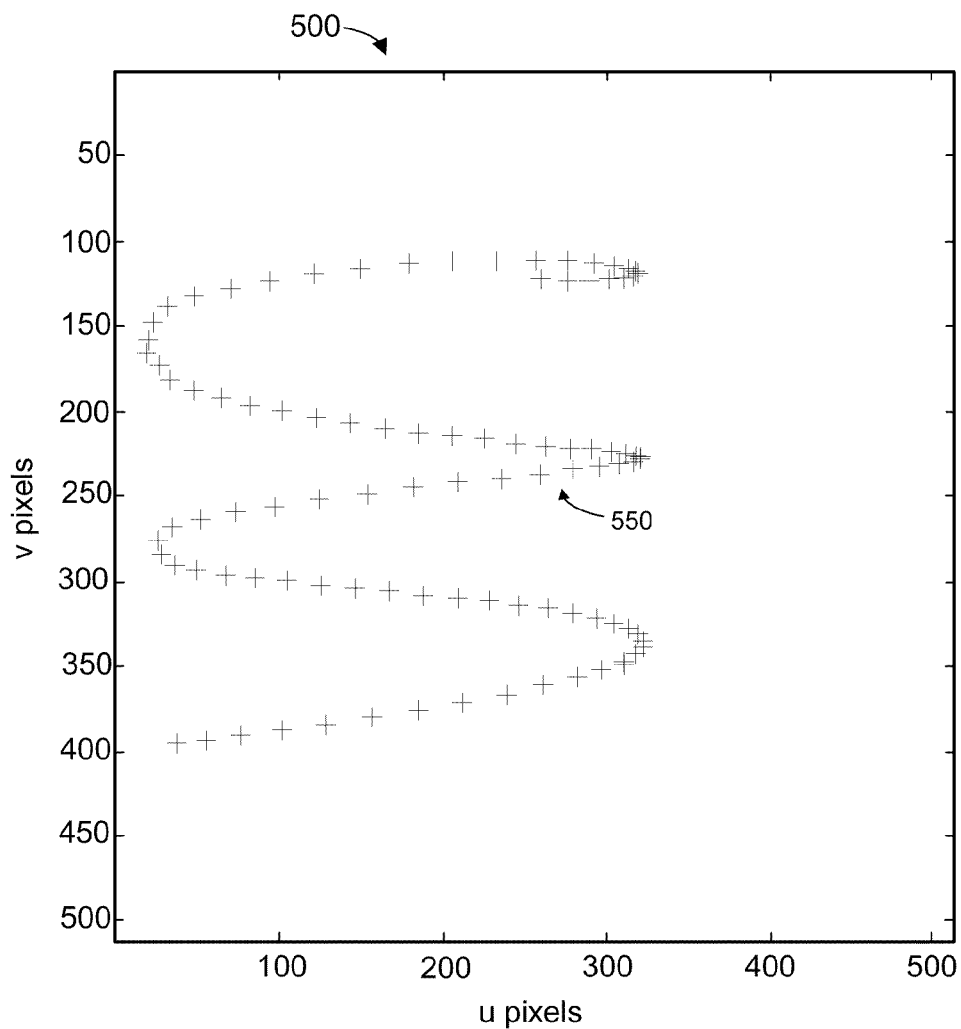
FIG. 5 is a representation of a calculated projection image according to some embodiments.

FIG. 5 is a representation of calculated projection image 500 determined at S201 based on the changed imaging geometry parameters according to some embodiments. Calculated projection image 500 includes pixels 550 associated with markers 145 of phantom 140. The difference between calculated projection image 500 and calculated projection image 300 of FIG. 3 is caused by the change in imaging geometry parameters, since the virtual model of the phantom is unchanged.

Figure 6:
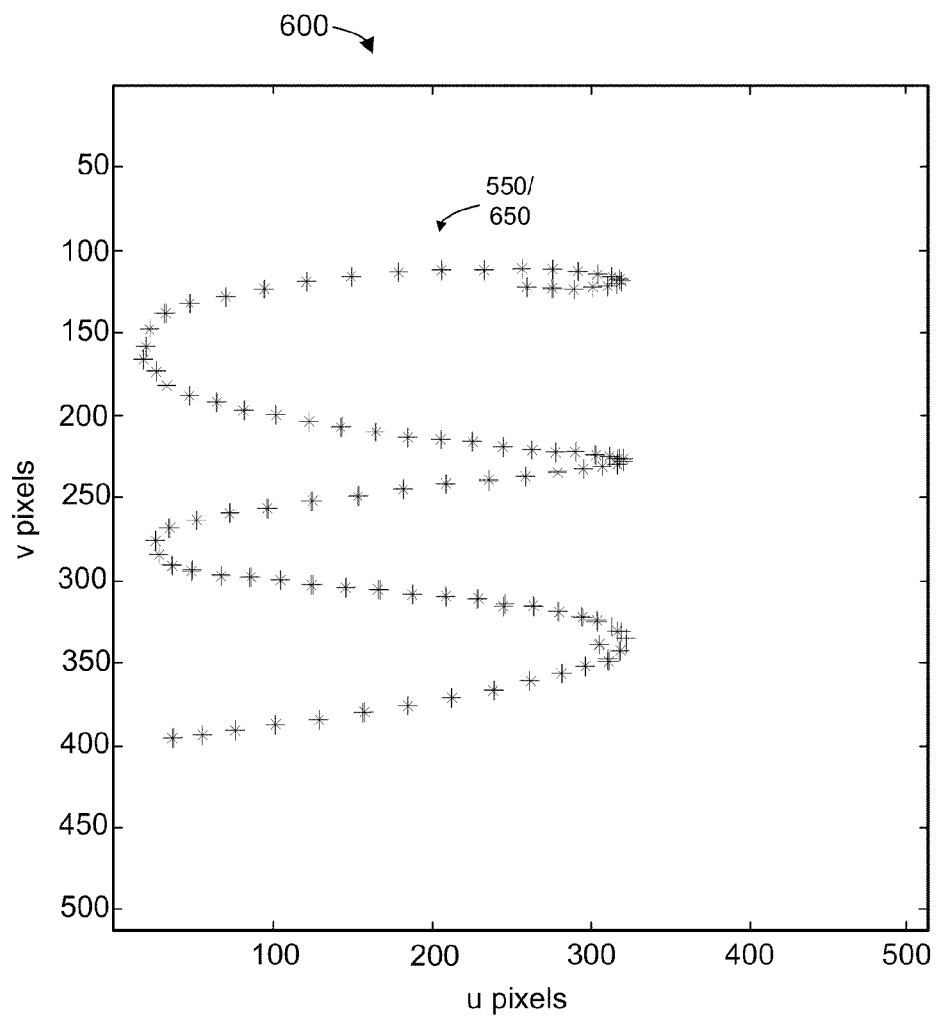
FIG. 6 is a representation of the FIG. 5 calculated projection image and a corresponding acquired projection image according to some embodiments.

Flow continues as described above to acquire a next acquired projection image at S202. The next acquired projection image is acquired while phantom 140 remains at the position maintained during acquisition of the prior acquired projection image. FIG. 6 shows acquired projection image 600 according to the present example. Pixels 650, indicating the locations of markers 145, match quite closely with pixels 550 of projection image 500, which are superimposed thereon.

Accordingly, it is determined at S204 that the difference between projection image 500 and projection image 600 is less than a threshold. Of course, some embodiments may require more than two iterations of S201 through S204 to achieve a difference less than the threshold.

At S206, it is determined whether the first radiation-based imaging system is to acquire additional types of projections (e.g., from other projection angles). If so, flow returns to S201 and proceeds as described above to determine imaging geometry parameters for an additional type of projection (e.g., a different projection angle). Initially, and as described above, a calculated projection image may be determined at S201 using default imaging geometry parameters associated with the additional type of projection.

After imaging geometry parameters are determined for each projection type of the first imaging system, the imaging geometry parameters are associated with the current (i.e., first) imaging system at S207. This association, as described in the background, may be subsequently used to reconstruct three-dimensional images based on projection images acquired by the current (i.e., first) imaging system.

In some embodiments, S201 is performed to determine a calculated projection image for each type of projection (e.g., projection angle) based on an overall model of imaging geometry parameters for each type of projection, and S202 is then performed to acquire a projection image from each projection angle. The overall model of imaging geometry parameters is then changed based on all the differences between each calculated projection image and its corresponding acquired projection image.

At S208, it is determined whether more imaging systems remain to be calibrated. If so, flow returns to S201 to determine a calculated projection image based on imaging geometry parameters associated with a next radiation-based imaging system (e.g., an imaging system including x-ray sources 119 and imaging system 117) and on the virtual model of the phantom. In this regard, storage 134 may store initial imaging geometry parameters associated with the next radiation-based imaging system.

Flow then continues as described above with respect to the next imaging system. In some embodiments, a position of the phantom is not changed from the position used during calibration of the first imaging system. Once the difference between a current calculated projection image and a current acquired projection image is determined to be less than a threshold (which may differ from the threshold used for the first imaging system), the current imaging geometry parameters (i.e., the imaging geometry parameters used to determined the current calculated projection image) are associated with the second imaging system.

Flow terminates if no more imaging systems are to be calibrated. Some embodiments may therefore provide a single procedure to determining imaging geometry parameters of multiple imaging systems (e.g., on the same gantry) using a single calibration phantom.

Embodiments are not limited to the two types of imaging systems described above with respect to FIG. 1 and process 200. Imaging geometry parameters may be determined for any combinations of MV CBCT, kV CBCT, digital tomosynthesis (stationary or otherwise), or other types of imaging systems that are or become known.

Figure 7:
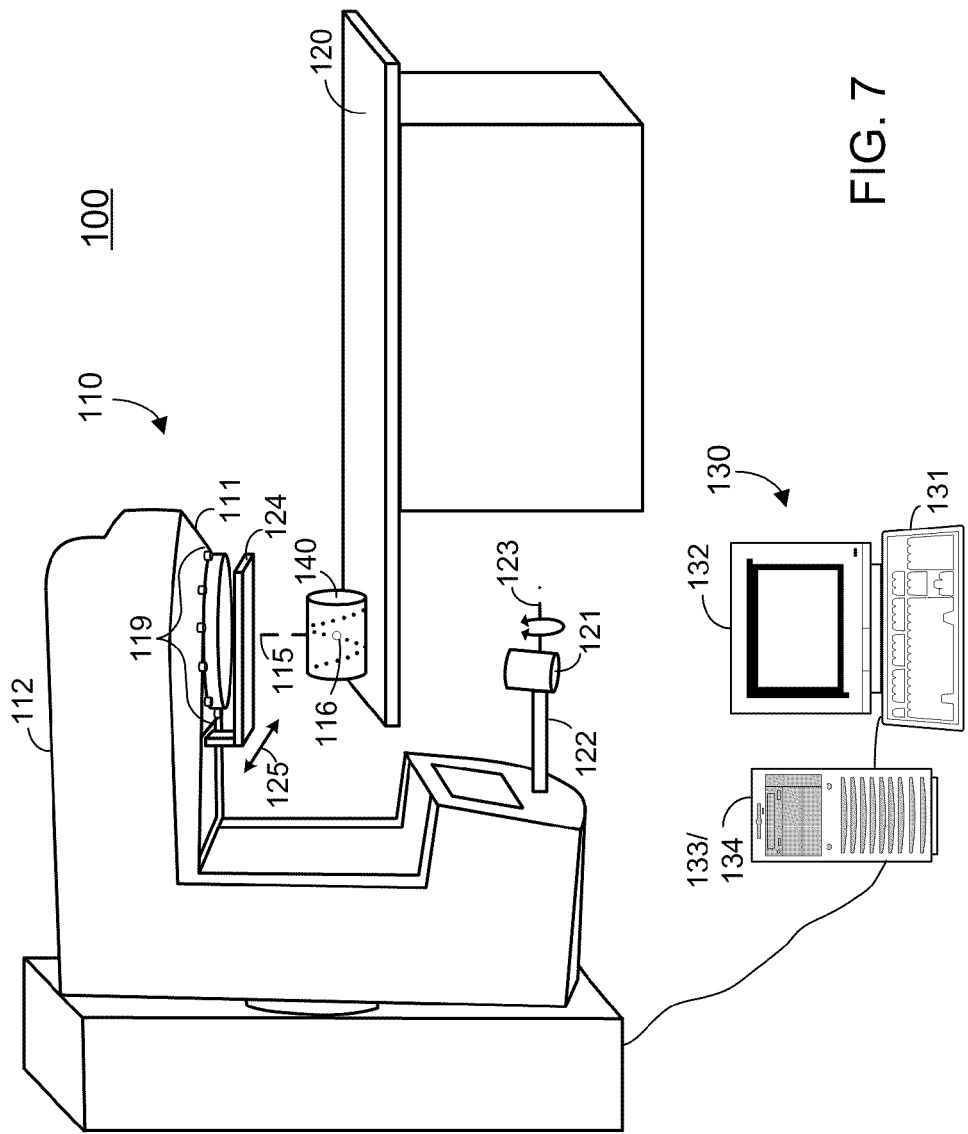
FIG. 7 is a perspective view of a linear accelerator system according to some embodiments.

For example, FIG. 7 illustrates the elements of treatment room 100 in a second configuration. Imaging device 117 has been retracted into a lower portion of gantry 112 and imaging x-ray source 121 has been extended therefrom. Also shown is x-ray detector 124 which has been deployed from a cavity of gantry 112 to a position in front of treatment head 111. Imaging x-ray source and x-ray detector 124 may comprise an imaging system that may be calibrated as described herein. Imaging x-ray source 121 and x-ray detector 124 comprise a tomosynthesis system. In other words, three-dimensional images may be reconstructed from projection images acquired using imaging x-ray source 121 and x-ray detector 124 by applying digital tomosynthesis algorithms thereto.

Imaging x-ray source 121 is coupled to gantry 112 via extension 122. In some embodiments, extension 122 may allow source 121 to rotate about axis 123 extending through source 121 and to translate in a plane perpendicular to beam axis 115. Source 121 may be coupled to extension 122 by a pivoting joint to allow such rotation. Imaging x-ray source 121 may comprise any suitable single or multi-source device to emit imaging radiation, including but not limited to a conventional x-ray tube. In some embodiments, x-ray source 121 emits kilovoltage radiation having energies ranging from 50 to 150 keV.

X-ray detector 124 is adapted to translate in a plane perpendicular to beam axis 115 as shown by arrow 125. In some embodiments, x-ray detector 124 is a flat-panel imaging device using a scintillator layer and solid-state amorphous silicon photodiodes deployed in a two-dimensional array. According to some embodiments, a single x-ray detector is used to acquire projection images based on x-rays emitted from a treatment delivering x-ray source (e.g., treatment head 111) and to acquire projection images based on x-rays emitted from a separate imaging x-ray source (e.g., imaging source 121).

For each imaging system to be calibrated, S201 through S206 may be repeated for each type of projection image that the system may acquire in order to determine imaging geometry parameters for each type of projection image. In the case of a CBCT imaging system, for example, S201 through S206 may be repeated for each gantry angle from which a projection image will be acquired during use. In the case of a stationary digital tomosynthesis system, S201 through S206 may be repeated for each x-ray source that will be used to acquire a projection image during use.

The several embodiments described herein are solely for the purpose of illustration. Therefore, persons in the art will recognize from this description that other embodiments may be practiced with various modifications and alterations.

What is claimed is:

1. A method comprising:
    determining a first projection image of a phantom based on first imaging geometry parameters associated with a first radiation-based imaging system and on a virtual model of the phantom;
    acquiring a second projection image of the phantom based on radiation emitted from the first radiation-based imaging system, the phantom located at a first position;
    determining a difference between the first projection image and the second projection image;
    determining second imaging geometry parameters based on the first imaging geometry parameters and the difference between the first projection image and the second projection image;
    determining a third projection image of the phantom based on the second imaging geometry parameters and on the virtual model of the phantom;
    acquiring a fourth projection image of the phantom located at the first position based on radiation emitted from the first radiation-based imaging system;
    determining a difference between the third projection image and the fourth projection image; and
    determining that the difference between the third projection image and the fourth projection image is less than a threshold.

2. A method according to claim 1, wherein determining the second imaging geometry parameters comprises:
    perturbing the first imaging geometry parameters based on the difference between the first projection image and the second projection image.

3. A method according to claim 1, comprising:
    determining a fifth projection image of the phantom based on third imaging geometry parameters associated with a second radiation-based imaging system and on the virtual model of the phantom;
    acquiring a sixth projection image of the phantom based on radiation emitted from the second radiation-based imaging system, the phantom located at the first position;
    determining a difference between the fifth projection image and the sixth projection image;
    determining fourth imaging geometry parameters based on the third imaging geometry parameters and the difference between the fifth projection image and the sixth projection image;
    determining a seventh projection image of the phantom based on the fourth imaging geometry parameters and on the virtual model of the phantom;
    acquiring an eighth projection image of the phantom located at the first position based on radiation emitted from the second radiation-based imaging system;
    determining a difference between the seventh projection image and the eighth projection image; and
    determining that the difference between the seventh projection image and the eighth projection image is less than a second threshold.

4. A method according to claim 3, wherein the first radiation-based imaging system comprises a kilovoltage cone beam computed tomography system, and
    wherein the second radiation-based imaging system comprises a megavoltage cone beam computed tomography system.

5. A method according to claim 4, wherein the first position is a radiation treatment isocenter associated with a linear accelerator.

6. A method according to claim 4, wherein the first radiation-based imaging system comprises a tomosynthesis imaging system, and
    wherein the second radiation-based imaging system comprises a megavoltage cone beam computed tomography system.

7. A method according to claim 6, wherein the first position is a radiation treatment isocenter associated with a linear accelerator.

8. A method according to claim 3, wherein the first radiation-based imaging system comprises a tomosynthesis imaging system, and
    wherein the second radiation-based imaging system comprises a kilovoltage cone beam computed tomography system.

9. A method according to claim 1, wherein the first position is a radiation treatment isocenter associated with a linear accelerator.

10. A method according to claim 1, wherein determining the second imaging geometry parameters based on the first imaging geometry parameters and the difference between the first projection image and the second projection image comprises:
    determining the second imaging geometry parameters to minimize the function $\Sigma_{u,v}[f_a(u,v)-f_m(u,v)]^2$,
    where $(u, v)$ are image pixel coordinates, $f_m(u,v)$ is the first projection image, and $f_a(u,v)$ is the second projection image.

11. A system comprising:
    a first radiation-based imaging system to emit radiation; and
    a processing device to:
        determine a first projection image of a phantom based on first imaging geometry parameters associated with the first radiation-based imaging system and on a virtual model of the phantom;
        acquire a second projection image of the phantom based on radiation emitted from the first radiation-based imaging system, the phantom located at a first position;
        determine a difference between the first projection image and the second projection image;
        determine second imaging geometry parameters based on the first imaging geometry parameters and the difference between the first projection image and the second projection image;
        determine a third projection image of the phantom based on the second imaging geometry parameters and on the virtual model of the phantom;
        acquire a fourth projection image of the phantom located at the first position based on radiation emitted from the first radiation-based imaging system;
        determine a difference between the third projection image and the fourth projection image; and
        determine that the difference between the third projection image and the fourth projection image is less than a threshold.

12. A system according to claim 11, wherein determination of the second imaging geometry parameters comprises:
    perturbing the first imaging geometry parameters based on the difference between the first projection image and the second projection image.

13. A system according to claim 11, further comprising:
a second radiation-based imaging system,
the processing device further to:
determine a fifth projection image of the phantom based on third imaging geometry parameters associated with the second radiation-based imaging system and on the virtual model of the phantom;
acquire a sixth projection image of the phantom based on radiation emitted from the second radiation-based imaging system, the phantom located at the first position;
determine a difference between the fifth projection image and the sixth projection image;
determine fourth imaging geometry parameters based on the third imaging geometry parameters and the difference between the fifth projection image and the sixth projection image;
determine a seventh projection image of the phantom based on the fourth imaging geometry parameters and on the virtual model of the phantom;
acquire an eighth projection image of the phantom located at the first position based on radiation emitted from the second radiation-based imaging system;
determine a difference between the seventh projection image and the eighth projection image; and
determine that the difference between the seventh projection image and the eighth projection image is less than a second threshold.

14. A system according to claim 13, wherein the first radiation-based imaging system comprises a kilovoltage cone beam computed tomography system, and
wherein the second radiation-based imaging system comprises a megavoltage cone beam computed tomography system.

15. A system according to claim 14, wherein the first position is a radiation treatment isocenter associated with a linear accelerator.

16. A system according to claim 13, wherein the first radiation-based imaging system comprises a tomosynthesis imaging system, and
wherein the second radiation-based imaging system comprises a megavoltage cone beam computed tomography system.

17. A system according to claim 16, wherein the imaging isocenter is a radiation treatment isocenter associated with a linear accelerator.

18. A system according to claim 13, wherein the first radiation-based imaging system comprises a tomosynthesis imaging system, and
wherein the second radiation-based imaging system comprises a kilovoltage cone beam computed tomography system.

19. A system according to claim 11, wherein the first position is a radiation treatment isocenter associated with a linear accelerator.

20. A system according to claim 11, wherein determination of the second imaging geometry parameters based on the first imaging geometry parameters and the difference between the first projection image and the second projection image comprises:
determining the second imaging geometry parameters to minimize the function $\Sigma_{u,v}[f_a(u,v)-f_m(u,v)]^2$,
where $(u, v)$ are image pixel coordinates, $f_m(u,v)$ is the first projection image, and $f_a(u,v)$ is the second projection image.

* * * * *